(12) United States Patent
Strand et al.

(10) Patent No.: US 11,622,925 B2
(45) Date of Patent: *Apr. 11, 2023

(54) DENTIFRICE COMPOSITIONS FOR TREATMENT OF DENTAL BIOFILM

(71) Applicant: The Procter & Gamble Company, Cincinnati, OH (US)

(72) Inventors: Ross Strand, Singapore (SG); Xiaoxiao Li, Beijing (CN); Yunming Shi, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/024,838

(22) Filed: Sep. 18, 2020

(65) Prior Publication Data

US 2021/0093527 A1    Apr. 1, 2021

(30) Foreign Application Priority Data

Sep. 30, 2019    (WO) ................ PCT/CN2019/109455

(51) Int. Cl.
| | |
|---|---|
| A61Q 11/00 | (2006.01) |
| A61K 8/21 | (2006.01) |
| A61K 8/27 | (2006.01) |
| A61K 6/00 | (2020.01) |
| A61K 8/60 | (2006.01) |
| A61K 8/365 | (2006.01) |
| A61K 8/44 | (2006.01) |
| A61K 8/25 | (2006.01) |
| A61K 8/34 | (2006.01) |

(52) U.S. Cl.
CPC ............. *A61K 8/27* (2013.01); *A61K 8/21* (2013.01); *A61K 8/25* (2013.01); *A61K 8/345* (2013.01); *A61K 8/365* (2013.01); *A61K 8/44* (2013.01); *A61K 2800/28* (2013.01); *A61K 2800/48* (2013.01)

(58) Field of Classification Search
CPC ........ A61K 2300/00; A61K 8/21; A61K 8/27; A61K 2800/48; A61K 8/25; A61K 2800/92; A61K 2800/28; A61K 2800/30; A61K 2800/592; A61K 8/60; A61Q 11/00; A61Q 17/005
See application file for complete search history.

(56) References Cited

U.S. PATENT DOCUMENTS

| | | | |
|---|---|---|---|
| 3,935,305 A | 1/1976 | Delaney | |
| 4,339,432 A * | 7/1982 | Ritchey ................ | A61K 8/27 424/49 |
| 4,363,794 A | 12/1982 | Ochiai | |
| 5,281,410 A | 1/1994 | Lukacovic | |
| 6,309,835 B1 | 10/2001 | Iyer | |
| 6,607,711 B2 | 8/2003 | Pedersen | |
| 6,846,478 B1 | 1/2005 | Doyle et al. | |
| 8,283,135 B2 | 10/2012 | Doyle | |
| 8,652,495 B2 | 2/2014 | Porter | |
| 8,691,190 B2 | 4/2014 | Haught | |
| 9,532,932 B2 | 1/2017 | Prencipe | |
| 9,883,995 B2 | 2/2018 | Prencipe | |
| 9,962,322 B2 | 5/2018 | Vemishetti et al. | |
| 10,105,303 B2 | 10/2018 | Pan | |
| 10,596,088 B2 | 3/2020 | Strand | |
| 10,596,089 B2 | 3/2020 | Strand | |
| 10,603,263 B2 | 3/2020 | Strand | |
| 10,813,863 B2 | 10/2020 | Strand | |
| 10,813,864 B2 | 10/2020 | Strand | |
| 2003/0157145 A1 | 8/2003 | Kalili | |
| 2004/0042978 A1 | 3/2004 | Embro | |
| 2006/0134020 A1* | 6/2006 | Robinson ................ | A61K 8/21 424/52 |
| 2009/0136432 A1 | 5/2009 | Strand et al. | |
| 2009/0186090 A1 | 7/2009 | Zaidel | |
| 2009/0202450 A1 | 8/2009 | Prencipe | |
| 2009/0202451 A1 | 8/2009 | Prencipe | |
| 2010/0322987 A1 | 12/2010 | Robinson | |
| 2010/0322988 A1 | 12/2010 | Prencipe | |
| 2010/0330003 A1 | 12/2010 | Robinson | |
| 2011/0052509 A1 | 3/2011 | Subramanyam | |
| 2011/0104081 A1 | 5/2011 | Scott | |
| 2012/0014883 A1 | 1/2012 | Scott | |
| 2012/0082630 A1 | 4/2012 | Haught | |
| 2012/0201762 A1 | 8/2012 | Pilch et al. | |
| 2013/0142736 A1 | 6/2013 | Robinson | |
| 2015/0297477 A1 | 10/2015 | Poth | |
| 2015/0297500 A1 | 10/2015 | Robinson | |
| 2015/0313813 A1 | 11/2015 | Rege | |
| 2016/0296437 A1* | 10/2016 | Yang ....................... | A61K 8/27 |
| 2017/0020801 A1 | 1/2017 | Santarpia | |

(Continued)

FOREIGN PATENT DOCUMENTS

| | | | |
|---|---|---|---|
| CN | 20110133194 A | 6/2010 | |
| CN | 106075545 A | 6/2016 | |

(Continued)

OTHER PUBLICATIONS

PCT/CH2017/075532 with written opinion; dated Apr. 21, 2017, 4 pages.
PCT Search Report and Written Opinion for PCT/CN2018/081054 dated Mar. 29, 2018.
Supplemental PCT Search Report for PCT/CN2018/081054 dated Mar. 29, 2018.
PCT Search Report and Written Opinion.
PCT Search Report and Written Opinion for PCT/CN2018/081107 dated Mar. 29, 2018.
PCT Search Report and Written Opinion for PCT/CN2018/081109 dated Mar. 29, 2018.
http://www.colgatetotal.com/total-benefits/whole-mouth-health/gingivitis-control.
The EPS Matrix: The "House of Biofilm Cells"; Hans-Curt Flemming, Thomas R. Neu2 and Daniel J. Wozniak; J. Bacteriol. 2007, 189(22):7945.

(Continued)

*Primary Examiner* — Tracy Liu
(74) *Attorney, Agent, or Firm* — Elizabeth A. Conklin

(57) ABSTRACT

Dentifrice compositions comprising zinc lactate, glycine, and fluoride ion are provided for treating dental plaque biofilm.

12 Claims, 2 Drawing Sheets

(56) References Cited

U.S. PATENT DOCUMENTS

| | | |
|---|---|---|
| 2017/0056531 A1 | 3/2017 | Shi |
| 2017/0100312 A1 | 4/2017 | Prencipe |
| 2017/0319444 A1 | 11/2017 | Dehghan |
| 2017/0348206 A1 | 12/2017 | Vemishetti |
| 2017/0348550 A1 | 12/2017 | Josias |
| 2018/0072944 A1 | 3/2018 | Shi |
| 2019/0298620 A1 | 10/2019 | Strand |
| 2019/0298634 A1 | 10/2019 | Strand |
| 2019/0298635 A1 | 10/2019 | Strand |
| 2019/0298636 A1 | 10/2019 | Strand |
| 2020/0093715 A1 | 3/2020 | Basa |
| 2020/0146958 A1 | 5/2020 | Strand |

FOREIGN PATENT DOCUMENTS

| | | |
|---|---|---|
| CN | 108743424 A | 11/2018 |
| EP | 0311260 B1 | 12/1994 |
| EP | 0740932 B1 | 9/2002 |
| EP | 1203575 B1 | 9/2010 |
| EP | 1843741 B1 | 4/2013 |
| EP | 2753292 B1 | 6/2018 |
| JP | 636613 B2 | 8/2018 |
| WO | 8600004 A1 | 1/1986 |
| WO | 2012057739 | 5/2012 |
| WO | 2014169085 | 10/2014 |
| WO | 2016176180 | 3/2016 |
| WO | 2016172334 A1 | 10/2016 |
| WO | 2016178652 A1 | 11/2016 |
| WO | 2017222548 A1 | 12/2017 |

OTHER PUBLICATIONS

Xiang J, Li H, Pan B, Chang J, He Y, He T, Strand R, Shi Y, Dong W. (2018) Penetration and Bactericidal Efficacy of Two Oral Care Products in an Oral Biofilm Model. Am J Dent, vol. 31, Issue 1: 53-60.

PCT Search Report and Written Opinion for PCT/CN2019/109455 dated Apr. 15, 2021, 11 pages.

AA01371F PCT Suppl. Search Report and Written Opinion for PCT/CN2019/109455 dated Jan. 3, 2022, 12 pages.

Database GNPD [Online] Mintel anonymous: "Anti-Bacterial Tooth paste",XP055873203, Database accession No. 1815817, Jun. 13, 2012, pp. 1-3.

Database GNPD [Online] Mintel; anonymous: "Day & Night Care Advanced Protection Toothpaste with Swiss Herb & Zinc Mineral", XP055675318, Database accession No. 6755931, Aug. 1, 2019, pp. 1-4.

Database GNPD [Online] Mintel; anonymous: "Toothpaste Repackaging", XP055871 929, Database accession No. 702070, May 14, 2007, pp. 1-2.

Database GNPD [Online] Mintel; anonymous: "Toothpaste with Fluoride",XP055873049, Database accession No. 1601978, Aug. 3, 2011, pp. 1-3.

Database GNPD [Online] Mintel; anonymous: "Toothpaste", XP055809295, Database accession No. 85453, Jan. 29, 2001, pp. 1-2.

* cited by examiner

DENTIFRICE COMPOSITIONS FOR TREATMENT OF DENTAL BIOFILM

FIELD OF THE INVENTION

The present invention relates to dentifrice compositions having improved efficacy to help inhibit biofilm formation or help disrupt biofilm.

BACKGROUND OF THE INVENTION

Dental plaque (also known as dental biofilm) is a sticky, colorless deposit of bacteria that is constantly forming on the tooth surface. Dental plaque is generally made up of bacteria and extracellular polymer substances (so called "EPS"). EPS are biopolymers of microbial origin in which biofilm microorganisms are embedded. *J. Bacteriol.* 2007, 189(22):7945. Saliva, food and fluids combine to produce these deposits that collect where the teeth and gums meet. Plaque buildup is the primary factor in poor oral health that can lead to caries and periodontal (gum) disease, including gingivitis. One way that dentifrice compositions help to prevent and control plaque is by leveraging anti-bacterial agents such as zinc ion source. However, the disadvantage or formulation challenge is the unintended reactivity of anti-bacterial agents with formulation ingredients and environment of dentifrice matrix. This may include oxidative degradation, hydrolysis, adsorption or precipitation of oxy-hydroxide species, any of which can impact the bio-availability of the anti-bacterial agent. Another problem of formulating a zinc containing dentifrice is astringency, an organoleptically displeasing effect on the zinc ion. Therefore, there is a continuing need to provide a dentifrice formulation that help prevent plaque formation on teeth, and at the same time having reduced astringency.

SUMMARY OF THE INVENTION

The present invention is based on the surprising discovery that the combination of zinc lactate and glycine in a dentifrice composition helps the disruption and destabilization of the biofilm EPS architecture. It is further surprisingly found that the penetration depth and/or penetration rate of zinc ion into the biofilms is increased, when used in combination with glycine. Further, the use of the glycine improves the sensorial experience reducing the associated astringency and metallic taste of zinc that will ensure product compliance and usage habit to deliver the oral health benefits.

An advantage of the present invention is the dentifrice composition of the present invention containing zinc lactate and glycine, intend to destabilize and disrupt the biofilm EPS architecture to aid the delivery and penetration of actives to biofilms for optimizing efficacy.

Another advantage of the present invention is, as a result of the destabilized dental biofilm (reduced thickness, bio-volume and increased porosity), it leads to improved delivery of the fluoride ion to the tooth surface to aid with the enamel remineralization cycle.

Yet another advantage of the present invention is that the dentifrice composition can provide a reduced astringency, so as to provide the consumer a better sensorial experience.

Still another advantage of the present invention is a phase stable formulation.

One aspect of the invention provides for a dentifrice composition comprising: a) from 0.2% to 2.0%, by weight of the composition, of a zinc lactate; b) from 0.1% to 6.0%, by weight of the composition, of a glycine or salt thereof, or combination thereof; and c) from 0.05% to 0.5%, by weight of the composition, of a fluoride ion.

Another aspect of the invention provides a method of treating dental biofilm comprising the step of brushing teeth with a composition of the present invention.

Yet another aspect of the invention provides a method reducing biofilm thickness and preventing or mitigating plaque formation on tooth enamel comprising the step of brushing teeth with a dentifrice composition of the present invention.

An advantage of the present invention is the relatively cost effectiveness of the formulation by relatively high level of water and minimizing other ingredients (such as humectants).

These and other features, aspects, and advantages of the present invention will become evident to those skilled in the art from the detailed description which follows.

BRIEF DESCRIPTION OF THE DRAWINGS

While the specification concludes with claims that particularly point out and distinctly claim the invention, it is believed the present invention will be better understood from the following description of the accompanying figures.

DETAILED DESCRIPTION OF THE INVENTION

Definitions

Figure 1:
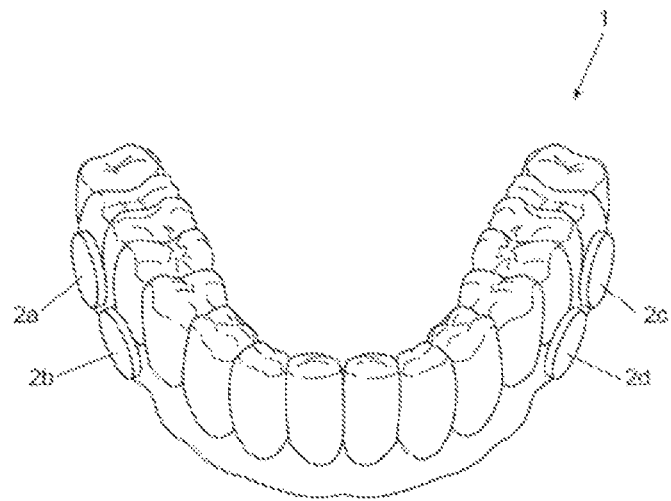
FIG. 1 is a perspective view of an oral splint with Hydroxyapatite ('HA') disks attached thereto.

As used herein, the articles including "a" and "an" when used in a claim, are understood to mean one or more of what is claimed or described.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "substantially free" as used herein refers to no intentional amount of that material is added to the composition or an amount of a material that is less than 0.05%, 0.01%, or 0.001% of the composition. The term "essentially free" as used herein means that the indicated material is not deliberately added to the composition, or preferably not present at analytically detectable levels. It is meant to include compositions whereby the indicated material is present only as an impurity of one of the other materials deliberately added. The term "free" as used herein refers to no reasonably detectable amount of that material is present in the composition.

The term "dentifrice" as used herein means paste, gel, powder, tablets, or liquid formulations, unless otherwise specified, that are used to clean the surfaces of the oral cavity. Preferably the dentifrice compositions of the present invention are single phase compositions. One example of a dentifrice is toothpaste (for brushing teeth). The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified.

All measurements referred to herein are made at 25° C. (i.e., room temperature) unless otherwise specified.

Dentifrice Compositions

It has been surprisingly discovered that the combination of zinc lactate and glycine in a dentifrice composition is particularly useful for treatment of dental biofilm. In particular, the surprising discovery is that the thickness of biofilm has been significantly reduced thus the penetration of the zinc ion into the biofilms is markedly improved when combined with glycine. Without wishing to be bound by theory, the neutral amino acid contains both carboxylic and amine groups. Zinc lactate is used as a desired anti-bacteria agent in the dentifrice formulation because the zinc is already combined with a suitable chelating agent in the form of a salt. The chelation of the zinc through lactate gives a controllable release of the $Zn^{2+}$ species, which are desired for the therapeutic effects. However, the associated $Zn^{2+}$ species impart a noticeable astringency of the sensorial experience. Surprisingly, the use of the glycine creates an ion exchange within the biofilm to reduce the Ca/EPS ratio, resulting in a reduction in biofilm thickness. It has also been surprisingly found that the penetration depth and/or the penetration rate of zinc ions into the biofilms may be increased, or markedly increased, when formulated with glycine. In short, the presence of glycine in combination with zinc lactate in a dentifrice composition aids the composition's efficacy in mediating the harmful effects of the bacteria in the biofilms on the gums. Such formulation also surprisingly reduces the sensorial astringency of the dentifrice.

In one aspect, the present invention is directed to a dentifrice composition comprising: a) from 0.2% to 2.0%, by weight of the composition, of a zinc lactate; b) from 0.1% to 6.0%, by weight of the composition, of a glycine or salt thereof, or combination thereof; and c) from 0.05% to 0.5%, by weight of the composition, of a fluoride ion.

In some examples, the zinc lactate is present in a level of from 0.4% to 1.8%, preferably from 0.5% to 1.5%, by weight of the composition. for example, zinc lactate can be present in the composition in a level of about 0.6%, or about 0.7%, or about 0.8%, or about 0.9%, or about 1.0%, or about 1.1%, or about 1.2%, or about 1.35, or about 1.3%, by weight of the composition.

Alternatively, the dentifrice composition may comprise a source of zinc ions sufficient to provide from 0.05% to 0.5%, preferably from 0.1% to 0.5%, or more preferably from 0.15% to 0.45% of soluble zinc ions by weight of the composition. For example, the dentifrice composition can comprise about 1000 ppm, or about 1500 ppm, or about 2000 ppm, or about 2500 ppm, or about 3000 ppm, or about 3500 ppm, or about 4000 ppm, by weight of the composition, of soluble zinc ion.

The dentifrice composition of the present invention may further comprise another zinc ion source selected from zinc organic salts, preferably selected from the group consisting of zinc citrate, zinc gluconate, and combinations thereof.

In some alternative examples, the dentifrice composition may further comprise insoluble or sparingly soluble zinc compounds, such as zinc oxide, zinc carbonate or zinc phosphate as the zinc ion source. But in other examples, the dentifrice composition does not comprise zinc oxide or other insoluble zinc salts such as zinc carbonate or zinc phosphate. In some alternative examples, the dentifrice composition may further comprise soluble zinc inorganic salts such as zinc chloride or zinc sulfate. But in other examples, the dentifrice composition does not comprise zinc inorganic salts such as zinc chloride or zinc sulphate, due to the unpleasant, astringent mouthfeel that the free zinc ions imparted.

Glycine

The dentifrice compositions of the present invention comprise glycine. The glycine can be present in its free form or suitable salts form. Suitable salts include salts known in the art to be pharmaceutically acceptable salts considered to be physiologically acceptable in the amounts and concentrations provided.

Preferably the glycine is present in the amount of from about 0.1% to about 6%, by weight of the composition. Preferably, the glycine is present in the amount of from about 0.5% to about 5%, more preferably from about 0.8% to about 4%, by weight of the composition.

It has been surprisingly discovered that the presence of glycine in a zinc containing formulation help to increase the penetration depth and/or penetration rate of zinc ion into the biofilms. Further, the use of glycine improves the sensorial experience by reducing the associated astringency and metallic taste of zinc that will ensure product compliance and usage habit to deliver the oral health benefits. Moreover, without wishing to be bound by theory, the presence of glycine may further lead to improved delivery of the fluoride ions source to the tooth surface, as a result of the destabilized dental biofilm, which could further aid with the enamel remineralization cycle.

Fluoride Ions

Preferably, the dentifrice compositions comprise a fluoride ion source as anti-caries agent. Suitable examples of fluoride ions may be selected from a source comprising stannous fluoride, sodium fluoride, potassium fluoride, sodium monofluorophosphate ("MFP"), indium fluoride, amine fluoride, zinc fluoride, and mixtures thereof. Preferably, the fluoride ion source is selected from sodium fluoride, stannous fluoride, MFP, or combinations thereof. The fluoride ion source may be present in an amount of from 0.0025% to 5%, or from 0.05% to 4%, or from 0.1% to 2%, or preferably from 0.2% to 1.5%, by weight of the composition, to provide anti-caries effectiveness. In certain examples, the fluoride ion source can be present in an amount sufficient to provide fluoride ions concentration in the composition at levels from 25 ppm to 25,000 ppm, generally at least from 500 ppm to 1600 ppm, for example 1100 ppm or 1450 ppm. The appropriate level of fluoride will depend on the particular application. A toothpaste for general user would typically have about 1000 ppm to 1500 ppm, with pediatric toothpaste having somewhat less.

Other Active Agents

The dentifrice compositions of the present invention may comprise a stannous ion source. In some examples, the stannous ion source may be present in the amount of from about 0.01% to about 5%, preferably from about 0.05% to about 4%, or more preferably from about 0.1% to about 2%, by weight of the composition, to provide anti-bacterial effectiveness. The stannous ion source used herein may include any safe and effective stannous salt. Suitable examples of stannous ion source are selected from the group consisting of stannous chloride, stannous fluoride, stannous acetate, stannous gluconate, stannous oxalate, stannous sulfate, stannous lactate, stannous tartrate, stannous iodide, stannous chlorofluoride, stannous hexafluorozirconate, stannous citrate, stannous malate, stannous glycinate, stannous carbonate, stannous phosphate, stannous pyrophosphate, stannous metaphosphate, and combinations thereof. Preferably, the stannous ion source is selected from stannous fluoride, stannous chloride, and combinations thereof. In one preferred example, the stannous ion source comprises stannous chloride. In another preferred example, the stannous ion source comprises stannous fluoride.

Alternatively, the dentifrice composition is substantially free of stannous ion source, preferably essentially free of stannous ion source, more preferably free of stannous ion source.

The dentifrice compositions of the present invention may optionally also include other anti-bacterial agents, preferably present in an amount of from 0.035% or more, from 0.05% to 2%, from 0.1% to 1%, by weight of the composition. Examples of these other anti-bacterial agents may include non-cationic anti-bacterial agents such as, for example, halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Other useful anti-bacterial agents are enzymes, including endoglycosidase, papain, dextranase, mutanase, and combinations thereof.

pH

The pH of the dentifrice composition of the present invention may be from pH 5.0 to 10.5, preferably from 5.5 to 8.0, more preferably from 6.0 to 7.8. In some preferred examples, the pH of the dentifrice compositions may be from pH 5.5 to 8.5. Alternatively, the dentifrice composition may have a pH of from 6 to 9, or from 6.5 to 8. In some examples, the pH is from 5.5 to 7.8, alternatively from pH 6.0 to pH 7.5, e.g., pH 7.7, or pH 7.6, or pH 7.5, or pH 7.4, or pH 7.3, or pH 7.2, or pH 7.1, or pH 7.0, or pH 6.9, or pH 6.8, or pH 6.7, or pH 6.6, or pH 6.5, or pH 6.4, or pH 6.3, or pH 6.2, or pH 6.1, or pH 6.0, or pH 5.9, or pH 5.8, or pH 5.7, or pH 5.6, or pH 5.5.

The pH is typically measured using a ratio of 1:3 of paste:water, whereby 1 gram of the dentifrice composition (e.g., toothpaste) is mixed into 3 grams of deionized water, and then the pH is assessed with an industry accepted pH probe that is calibrated under ambient conditions. The pH is measured by a pH meter with Automatic Temperature Compensating (ATC) probe. For purposes of clarification, although the analytical method describes testing the dentifrice composition when freshly prepared, for purposes of claiming the present invention, the pH may be taken at any time during the product's reasonable lifecycle (including but not limited to the time the product is purchased from a store and brought to the user's home).

After each usage the electrode should be washed free from the sample solution with water. Remove any excess water by wiping with a tissue, such as Kimwipes or equivalent. When electrode is not in use, keep electrode tip immersed in pH 7 buffer solution or electrode storage solution. Equipment details are as follows:

pH Meter: Meter capable of reading to 0.01 or 0.001 pH units.
Electrode: Orion Ross Sure-Flow combination: Glass body—VWR #34104-834/Orion #8172BN or VWR #10010-772/Orion #8172BNWP.
  Epoxy body—VWR #34104-830/Orion #8165BN or VWR #10010-770/Orion #8165BNWP.
  Semi-micro, epoxy body—VWR #34104-837/Orion #8175BN or VWR #10010-774/Orion #3175BNWP.
  Orion PerpHect combination: VWR #34104-843/Orion #8203BN semi-micro, glass body.
ATC Probe: Fisher Scientific, Cat. #13-620-16.

pH Modifying Agent

The dentifrice compositions herein may optionally include an effective amount of a pH modifying agent, alternatively wherein the pH modifying agent is a pH buffering agent. The pH modifying agents, as used herein, refer to agents that can be used to adjust the pH of the dentifrice compositions to the above-identified pH range. The pH modifying agents include hydrochloric acid, alkali metal hydroxides, ammonium hydroxide, organic ammonium compounds, carbonates, sesquicarbonates, borates, silicates, phosphates, imidazole, and mixtures thereof.

Specific pH modifying agents include monosodium phosphate (monobasic sodium phosphate), trisodium phosphate (sodium phosphate tribasic dodecahydrate or TSP), sodium benzoate, benzoic acid, sodium hydroxide, potassium hydroxide, alkali metal carbonate salts, sodium carbonate, imidazole, pyrophosphate salts, polyphosphate salts both linear and cyclic form, sodium gluconate, lactic acid, sodium lactate, citric acid, sodium citrate, phosphoric acid.

Thickening Agent

The dentifrice compositions of the present invention may comprise a thickening agent. Preferably the dentifrice composition comprises from 0.1% to 5%, preferably from 0.8% to 3.5%, more preferably from 1% to 3%, yet still more preferably from 1.3% to 2.6%, by weight of the composition, of the thickening agent.

Preferably the thickening agent comprises a thickening polymer, a thickening silica, or a combination thereof. Yet more preferably, when the thickening agent comprises a thickening polymer, the thickening polymer is selected from a charged carboxymethyl cellulose, a non-ionic cellulose derivative, a linear sulfated polysaccharide, a natural gum, polymers comprising at least a polycarboxylated ethylene backbone, and combinations thereof.

In one example the thickening silica is obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167).

Preferably the linear sulfated polysaccharide is a carrageenan (also known as carrageenin). Examples of carrageenan include Kappa-carrageenan, Iota-carrageenan, Lambda-carrageenan, and combinations thereof.

In one example the CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A).

Preferably a natural gum is selected from the group consisting of gum karaya, gum arabic (also known as acacia gum), gum tragacanth, xanthan gum, and combination thereof. More preferably the natural gum is xanthan gum. Xanthan gum is a polysaccharide secreted by the bacterium

*Xanthomonas camestris*. Generally, xanthan gum is composed of a pentasaccharide repeat units, comprising glucose, mannose, and glucuronic acid in a molar ratio of 2:2:1, respectively. The chemical formula (of the monomer) is $C_{35}H_{49}O_{29}$. In one example, the xanthan gum is from CP Kelco Inc (Okmulgee, US).

Preferably, the non-ionic cellulose or derivative thereof has an average molecular weight range of 50,000 to 1,300,000 Daltons, and preferably an average degree of polymerization from 300 to 4,800. More preferably, the non-ionic cellulose or derivative thereof is hydroxyethyl cellulose ("HEC").

Preferably the polymer comprising at least a polycarboxylated ethylene backbone is selected from the group consisting of: co-polymers of maleic anhydride with methyl vinyl ether having a molecular weight of 30,000 to 1,000,000 Daltons; homo-polymers of acrylic acid; and co-polymers of maleic acid and acrylic acid or methacrylic.

The co-polymers of maleic anhydride with methyl vinyl ether are at least one of: Gantrez AN139 (M.W. 500,000 Daltons), Gantrez AN119 (M.W. 250,000 Daltons), or S-97 Pharmaceutical Grade (M.W. 70,000 Daltons); and the homo-polymers of acrylic acid and co-polymers of maleic acid and acrylic acid or methacrylic acid are at least one of: Acusol 445, Acusol 445N, Acusol 531, Acusol 463, Acusol 448, Acusol 460, Acusol 465, Acusol 490, Sokalan CP5, Sokalan CP7, Sokalan CP45, or Sokalan CP12S; and (v) combinations thereof.

In an example, the GANTREZ™ series of polymers are co-polymers of maleic anhydride with methyl vinyl ether having a molecular weight (M.W.) of 30,000 Daltons to 1,000,000 Daltons. These co-polymers are available for example as GANTREZ™ AN139 (M.W. 500,000 Daltons), AN119 (M.W. 250,000 Daltons) and S-97 Pharmaceutical Grade (M.W. 70,000 Daltons), from Ashland Chemicals (Kentucky, USA).

In another example, the ACUSOL™ and the SOKALAN series of polymers include homopolymers of acrylic acid and copolymers of maleic acid and acrylic acid or methacrylic. Examples are 0:1000 to 1000:0 copolymers of maleic acid with acrylic acid having a molecular weight (M.W.) of about 2,000 to about 1,000,000. These copolymers are commercially available as ACUSOL™ 445 and 445N, ACUSOL™ 531, ACUSOL™ 463, ACUSOL™ 448, ACUSOL™ 460, ACUSOL™ 465, ACUSOL™ 497, ACUSOL™ 490 from Dow Chemicals (Michigan, USA) and as Sokalan® CP 5, Sokalan® CP 7, Sokalan® CP 45, and Sokalan® CP 12 S from BASF (New Jersey, USA).

In another example, the crosslinked polyacrylic acid (PAA) polymer is a generic term for the synthetic high molecular weight polymers of acrylic acid. These may be homopolymers of acrylic acid, crosslinked with an allyl ether pentaerythritol, allyl ether of sucrose or allyl ether of propylene. And, in a water solution at neutral pH, PAA is an anionic polymer, i.e. many of the side chains of PAA will lose their protons and acquire a negative charge. Carbopol®-type polymers, such as Carbopol®, Pemulen® and Noveon®, are polymers of acrylic acid, crosslinked with polyalkenyl ethers or divinyl glycol. Carbomer commercial codes, e.g. 940™, indicate the molecular weight and the specific components of the polymer.

Humectants

The dentifrice compositions herein may include humectants present in the amount of from 0% to 70%, or from 15% to 55%, by weight of the compositions. Humectants keep dentifrice compositions from hardening upon exposure to air and certain humectants may also impart desirable sweetness of flavor to dentifrice compositions. Suitable examples of humectants may include glycerin, sorbitol, polyethylene glycol, propylene glycol, xylitol, trimethyl glycine, and mixtures thereof. Other examples may include other edible polyhydric alcohols. In some examples, the humectant is selected from sorbitol, glycerin, and combinations thereof. In a preferred example, the humectant is sorbitol. In another preferred example, the humectant is glycerin. In an example, the composition comprises from 10% to 66%, alternatively from 30% to 55%, of humectant by weight of the composition.

Water

Water is commonly used as a carrier material in dentifrice compositions due to its many benefits. For example, water is useful as a processing aid, is benign to the oral cavity and assists in quick foaming of toothpastes. Water may be added as an ingredient in its own right or it may be present as a carrier in other common raw materials such as, for example, sorbitol and sodium lauryl sulfate.

In some examples, the dentifrice compositions herein may include from 10% to 70%, or preferably from 15% to 30%, by weight of the composition, of total water content. The term "total water content" as used herein means the total amount of water present in the dentifrice composition, whether added separately or as a solvent or carrier for other raw materials but excluding that which may be present as water of crystallization in certain inorganic salts. Preferably, the water is USP water.

Alternatively, in other examples, the dentifrice compositions herein may include from 0% to 5%, by weight of the composition, of total water content. For example, the dentifrice composition may be substantially free of water, preferably free of water.

Surfactants

Optionally, but preferably, the dentifrice compositions comprise a surfactant. The surfactant may be selected from anionic, nonionic, amphoteric, zwitterionic, cationic surfactants, or combinations thereof, preferably the surfactant is anionic, more preferably the anionic surfactant is sodium lauryl sulfate (SLS). An example of a zwitterionic surfactant is cocamidopropyl betaine. The dentifrice composition may contain one, two, or more surfactants. The composition may include a surfactant at a level of from 0.1% to 20%, preferably from 1% to 10%, by weight of the total composition.

Abrasives

The dentifrice composition comprises an effective amount of an abrasive. Examples of abrasives include a calcium-containing abrasive, a silica, or combinations thereof. If containing a calcium-containing abrasive, the calcium-containing abrasive is preferably selected from the group consisting of calcium carbonate, dicalcium phosphate, tricalcium phosphate, calcium orthophosphate, calcium metaphosphate, calcium polyphosphate, calcium oxyapatite, sodium carbonate, sodium bicarbonate, and combinations thereof. If a silica, preferably the silica is a precipitated silica (e.g., sodium silicate solution by destabilizing with acid as to yield very fine particles) such as those from the ZEODENT® series from Huber Engineered Materials (e.g., ZEODENT® 103, 124, 113 115, 163, 165, 167). It is acknowledged that some of these silicas (e.g., synthetic amorphous silica) can perform both abrasive and thickening functions, but are included herein under the term "abrasive" for purposes of the present invention. Preferably the dentifrice composition comprises from 1% to 35%, more preferably from 5% to 25% of abrasive, by weight of the composition.

Flavoring Agent

The dentifrice composition herein may include from 0.01% to 5%, preferably from 0.1% to 2%, by weight of the composition, of a flavoring agent. Examples of suitable flavoring agent that may be used in the dentifrice composition include those described in U.S. Pat. No. 8,691,190; Haught, J. C., from column 7, line 61 to column 8, line 21. In some examples, the flavoring agent may be selected from methyl salicylcate, menthol, eugenol and cineol. In some examples, the dentifrice composition may comprise a flavor mixture which is free of or substantially free of methyl salicylcate, menthol, eugenol and cineol.

Sweetener

The dentifrice compositions herein may include a sweetening agent. The sweetening agent is generally present in the dentifrice compositions at levels of from 0.005% to 5%, by weight of the composition. Suitable examples of sweetener include saccharin, dextrose, sucrose, lactose, xylitol, maltose, levulose, aspartame, sodium cyclamate, D-tryptophan, dihydrochalcones, acesulfame, sucralose, neotame, and mixtures thereof. Other suitable examples of sweetener are described in U.S. Pat. No. 8,691,190; Haught, J. C. from column 9, line 18 to column 10, line 18.

Coloring Agents

The dentifrice compositions herein may include a coloring agent present in the amount of from 0.001% to 0.01%, by weight of the compositions. The coloring agent may be in the form of an aqueous solution, preferably 1% coloring agent in a solution of water. Suitable examples of coloring agents may include pigments, pealing agents, filler powders, talc, mica, magnesium carbonate, calcium carbonate, bismuth oxychloride, zinc oxide, and other materials capable of creating a visual change to the dentifrice compositions. Other suitable examples may include titanium dioxide ($TiO_2$). Titanium dioxide is a white powder which adds opacity to the compositions and is generally present in the dentifrice compositions at levels of from 0.25% to 5%, by weight of the composition.

Other Ingredients The present dentifrice composition can comprise the usual and conventional ancillary components that are known to one skilled in the art. Optional ingredients include, for example, but are not limited to, anti-plaque agent, anti-sensitivity agent, whitening and oxidizing agent, anti-inflammatory agent, anti-calculus agent, chelating agent, tooth substantive agent, analgesic and anesthetic agent. It will be appreciated that selected components for the dentifrice compositions must be chemically and physically compatible with one another.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Example A: Examples 1 to 3

Examples 1 is a reference to the Phosphate Buffer Solution, whereas Ex. 2 and Ex. 3 are dentifrice compositions. They may be suitably prepared by conventional methods chosen by the formulator. Example 2 is a comparative formulation and example 3 is an inventive composition comprising zinc lactate and glycine. All of the compositions are prepared by admixture of the components in Table 1, in the proportions indicated.

TABLE 1

Examples 1 to 3

| Ingredients | Ex. 1 | Ex. 2 (Comparative) | Ex. 3 (Inventive) |
| --- | --- | --- | --- |
| Sorbitol Solution 70% | — | 40.50 | 40.50 |
| Sodium Fluoride | — | 0.321 | 0.321 |
| Zinc Lactate Dihydrate | — | 1.10 | 1.10 |
| Zinc Citrate | — | — | — |
| Glycine | — | — | 2.00 |
| Hydroxyethyl Cellulose | — | 0.30 | 0.30 |
| Carrageenan Mixture Iota | — | 0.50 | 0.50 |
| Sodium CMC | — | 1.00 | 1.00 |
| Silica Abrasive | — | 20.00 | 20.00 |
| Sodium Lauryl Sulphate (28% soln.) | — | 7.50 | 7.50 |
| Sodium Saccharin | — | 0.40 | 0.40 |
| Flavor/sensate oils | — | 1.30 | 1.30 |
| Sodium Citrate | — | 0.274 | 0.274 |
| Sodium Hydroxide | — | — | 0.125 |
| Water and minors (e.g., color soln.) | — | q.s. | q.s. |
| NaCl | 0.800 | — | — |
| KCl | 0.020 | — | — |
| Na2HPO4 | 0.142 | — | — |
| KH2PO4 | 0.024 | — | — |
| Warer | 99.014 | — | — |
| Total | 100% | 100% | 100% |
| Target pH | 7.0 | 6.7 | 7.3 |

Example B—Assay for Measuring Biofilm Architecture, Penetration of Anti-Bacterial Agent & Endotoxin Neutralization in the Biofilms The following assay is used an in situ plaque biofilm for inventive dentifrice compositions of the present invention and controls in order to: (1) assess the biofilm EPS matrix destabilization and thickness of the dental biofilm by measuring fluorescent light emitted from the labeled EPS biofilm; and (2) assess penetration efficiency of zinc ions with bacteria via measurement of co-localization percentage.

Details of the assay are described below.

(a) Substrate for Biofilm Growth

Hydroxyapatite ("HA") disks are used for in situ growth of biofilms. The HA disks are designed having three parallel grooves (i.e., 200 μm wide; 200 μm deep for two sides' grooves; while 500 μm wide and 500 μm deep for the middle groove) in each disk. When attaching disks to subject's mouth, keep these grooves vertical, to mimic interproximal gap between teeth, which is the hard-to-clean area where plaque generally tends to accumulate. This model allows the collection of undisturbed plaque from the grooves. HA disks are manufactured by Shanghai Bei'erkang biomedicine limited company (Shanghai, China).

(b) Wearing the Splint

Figure 2:
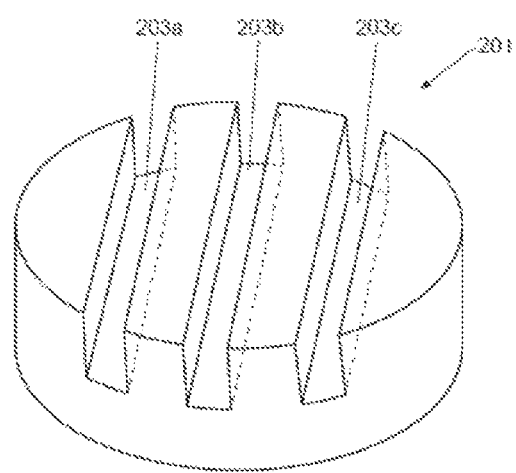
FIG. 2 is a perspective view of the HA disk having grooves therein.
Figure 3:
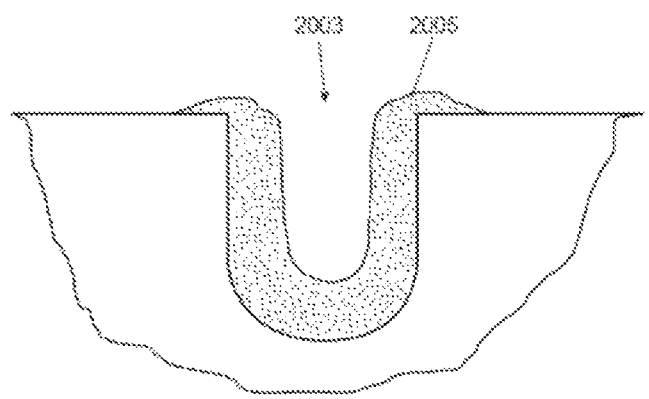
FIG. 3 is a schematic of a cross sectional view of the groove with biofilm therein.

Human subjects wear the splint. Each subject wears up to 12 HA disks on the splint to ensure that, at least, 9 HA disks are available after 48 hours. A non-limiting example of such a splint and HA disks are shown in FIG. 1. With reference to FIG. 1, the device (1) holds a plurality of HA disks (2a-2d). In a specific example, and with reference to FIG. 2, the HA disk (201) has three parallel grooves (203) (the two sides' grooves (203a and 203c) are 300 μm wide and 300 μm deep; while the middle grove (203b) (in between the two side grooves) is 500 μm wide and 500 μm deep). The middle groove is designed wider and deeper than the two sides' grooves so that the HA disk can be more easily separated into two identical half-disks for head-to-head comparison purposes. FIG. 3 is a schematic of a cross-sectional view of the groove (2003) with biofilm (2005) therein. Further details of the HA disks are described in US2017/0056531 (e.g. paragraphs [0019]-[0020]).

Although not shown in FIG. 3, the disks can be positioned such that the recede is in the inter-dental space between the teeth (since this location is prone to plaque (given the difficulty in cleaning, etc.)). The subjects withdraw the splint only during meals (the splint stored in an opaque container in humid conditions) and to perform oral hygiene procedures Immediately thereafter, the splint is worn again. Subjects are asked to use a straw when drinking.

(c) In-situ Biofilms Release From HA Desk

All HA disks are removed from the splint at 48 hours by tweezers. Tweezers are used to hold the edge of HA chips and transfer the HA disk to a 2 mL centrifuge tube containing PBS (phosphate buffered saline) solution. Tweezers are washed thoroughly (water; 75% alcohol; and then deionized water) before every disk transfer.

(d) Preparation of Toothpaste Supernatant 15 grams of deionized water is added to 5 grams toothpaste (using any one of the Examples 1-3). After stirring thoroughly, the mixture is centrifuge at 12,000 RPM for 20 minutes. The supernatant is prepared one day before usage and stored at 4° C.

(e) Confocal Laser Scanning Microscopy

After the HA disks are removed from the splint. The HA disks are used for ex vivo treatment by the different inventive and comparative compositions. After being treated with the subject supernatant and labeled with microbial fluorescent probe and stannous fluorescent probe (such as described in US2018/0072944A1; Shi et al.), the biofilms in the grooves are measured by confocal laser scanning microscopy ("CLSM") (as described below).

(f) Disk Preparation

The HA disks are rinsed in PBS solution and each HA disk is divided into two halves by tweezers. Thereafter, each half-disk is placed into 500-1000 μL of PBS solution statically for 1 minute. Each disk is treated for two minutes by either PBS solution or toothpaste supernatant. Each disk is washed by holding each disk with tweezers, shaken for ten rounds of back and forth in 1 mL of PBS solution, and then this washing cycle is repeated. Then each disk is immersed into 500-1000 μL PBS solution statically for 5 minutes.

After being treated with PBS and/or the oral care composition (e.g., toothpaste) supernatant and labeled with specific fluorescent probes, the biofilm in the grooves is measured by confocal laser scanning microscopy (CLSM).

(g) Fluorescence Probe Staining and Microscopy

"Ion fluorescent probe" means a fluorescent probe that specifically binds to one kind of ions and emit fluorescence at a certain wavelength. In recent years, significant emphasis has been placed on the development of new, highly selective fluorescent probes of ions because of their potential applications in biochemistry and environmental research. Many kinds of signaling mechanisms have been proposed and utilized for optical detection of ions, including photo-induced electron/energy transfer (PET), intramolecular charge transfer (ICT), fluorescence resonance energy transfer (FRET), and so on. Some of these fluorescent probes can also be applied in fluorescence bioimaging, which causes little cell damage and is highly sensitive with high-speed spatial analysis of living cells. Specifically, FRET imaging that affords simultaneous recording of two emission intensities at different wavelengths in the presence and absence of analytes has provided a facile method for visualizing complex biological processes at the molecular level. This technique appears to be suited to the study of physiological functions or pathogenesis of ions in biofilm and human body.

Zinc penetration efficiency of zinc ions with bacteria via measurement of co-localization percentage. Non-limiting examples of a zinc fluorescent probe suitable for labeling the biofilm may include any one following of the compounds:
2-(2(((1H-pyrrol-2-yl)methyl)amino)ethyl)-3',6'-diaminospiro[isoindoline-1,9'-xanthen]-3-one); (b) 2-(2(((1H-pyrrol-2-yl)methyl)amino)ethyl)-3',6'-bis(ethylamino)-2',7'-dimethylspiro[isoindoline-1,9'-xanthen]-3-one); (c) 2-(2-(((1H-pyrrol-2-yl)methyl)amino)ethyl)-3',6'-bis(diethylamino)spiro[isoindoline-1,9'-xanthen]-3-one; (d) 2-(2-(((1H-pyrrol-2-yl)methyl)amino)ethyl)-3',6'-bis(diethylamino)spiro[isoindoline-1,9'-xanthen]-3-one; (e) 2-(2-(((1H-pyrrol-2-yl)methyl)amino)ethyl)-3',6'-bis(phenylamino)spiro[isoindoline-1,9'-xanthen]-3-one; (f) 2-(2-(((1H-pyrrol-2-yl)methyl)amino)ethyl)-3',6'-di(pyrrolidin-1-yl)spiro[isoindoline-1,9'-xanthen]-3-one; (g) 2-(2-(((1H-pyrrol-2-yl)methyl)amino)ethyl)-3',6'-diamino-2',7'-diethylspiro[isoindoline-1,9'-xanthen]-3-one; (h) 2-(2-(((1H-pyrrol-2-yl)methyl)amino)ethyl)-2',7'-dibutyl-3',6'-bis(diethylamino)spiro[isoindoline-1,9'-xanthen]-3-one)-3-one; (i) 2-(2-(((1H-pyrrol-2-yl)methyl)amino)ethyl)-3',6'-dimorpholinospiro[isoindoline-1,9'-xanthen]-3-one; (j) 2-(2-(((1H-pyrrol-2-yl)methyl)amino)ethyl)-3',6'-di(piperidin-1-yl)spiro[isoindoline-1,9'-xanthen]-3-one; (k) 2-(2-(((1H-pyrrol-2-yl)methyl)amino)ethyl)-1',2',3',4',8',9',10',11'-octahydrospiro[isoindoline-1,6'-pyrano[3,2-g:6,6-g'] diquinolin]-3-one; (l) 2-(2-(((1H-pyrrol-2-yl)methyl)amino) ethyl)-1',2',3',4',10',11',12',13'-octahydrospiro[isoindoline-1,7'-pyrano[2,3-f:6,5-f']diquinolin]-3-one; (m) 2-(2(((1H-pyrrol-2-yl)methyl)amino)ethyl)-2',7'-dimethyl-3',6'-di (piperidin-1-yl)spiro[isoindoline-1,9'-xanthenl]-3-one) and (n) 2-(2(bis((1H-pyrrol-2-yl)methyl)amino)ethyl)-3',6'-bis (diethylamino)spiro[isoindoline-1,9'-xanthen]-3-one) .

Generally these zinc fluorescent probes contain a Rhodamine B derivative moiety as fluorophore, linked via amide moiety to 2-methyl 1H-pyrrole. Further details are described in the WO 2016/041138 A1.

The "Microbial fluorescent probe" means a fluorescent probe that binds to microbes of a biofilm and emit fluorescence at a certain wavelength. One class of such probes includes fluorescently labeled oligonucleotides, preferably rRNA-directed oligonucleotides. Non-limiting examples include SYTO™ branded dyes. One specific example is SYTO® 9 Green Fluorescent Nucleic Acid Stain, wherein excitation is a 485 (DNA) and 486 (RNA), and light emission is detected at 498 (DNA) and 501 (RNA).

After treatment and immersing, each half-disk is stained with the Zn probe together with Syto-9 probe (containing 5 μM Syto-9 and 5 μM Zn probe) for 30 minutes in the dark. The SYTO-9/Zn dye stained samples, the following parameters are used: $\lambda ex$=488 nm/560 nm, $\lambda em$=500/580 nm, 20× objective lens, and scanning from bottom of surface bacteria for 60 μm with step size=3 μm.

Fluorescence labeled calcium probes are molecules that exhibit an increase in fluorescence upon binding $Ca^{2+}$. The biofilm is labeled with a calcium fluorescent probe. Examples of a calcium fluorescent probe suitable for labeling the biofilm may be any one or more of the following compounds:

(a) Fluo-3™, AM™, cell permeant fluorescence stains;
(b) Fluo-3™, Pentapotassium Salt, cell impermeant fluorescence stains;
(c) Fluo-4™, AM™, cell permeant fluorescence stains;
(d) Fluo-4™, Pentapotassium Salt, cell impermeant fluorescence stains;
(e) Fluo-4 Direct™ Calcium Assay Kit;
(f) Mag-Fluo-4™, Tetrapotassium Salt, cell impermeant fluorescence stains; and
(g) Fluo-5F™, AM™, cell permeant fluorescence stains.
One or more of these probes may be available from ThermoFisher Scientific Company, Waltham, Mass.

Fluo-3™ is used to image the spatial dynamics of Ca2+ signaling. Biofilm may be treated with the AM™ ester forms of calcium probes by adding the dissolved probe directly to biofilm. Fluo-3™, AM™, cell permeant fluorescent probes are used for intracellular and extracellular calcium staining using confocal microscopy, flow cytometry, and microplate screening applications (absorption/emission maxima ~506/526 nm). It is reported that the Concanavalin A™ (Con A), Alexa Fluor® 594 Conjugate is a reliable alternative to stain EPS of biofilm. Alexa Fluor® 594 conjugate of Con A exhibits the bright, red fluorescence of the Alexa Fluor® 594 dye (absorption/emission maxima ~590/617 nm). Concanavalin A™, Alexa Fluor® 594 Conjugate selectively binds to α-mannopyranosyl and α-glucopyranosyl residues which are rich in EPS part of biofilm.

One specific example is Concanavalin A™, Fluorescein Conjugate™, wherein excitation is 494 nm, and maximum light emission is detected at 518 nm. These EPS fluorescent probes are widely available as well as the procedure details in how to use them to quantitatively determine the location and/or amount of EPS.

Examples of an EPS fluorescent probe suitable for labeling the biofilm may be any one of the following compounds:
(a) Molecular Probes™ Concanavalin A™ Alexa Fluor® 350 Conjugate™;
(b) Molecular Probes™ Concanavalin A™ Alexa Fluor® 488 Conjugate™;
(c) Molecular Probes™ Concanavalin A™ Alexa Fluor® 594 Conjugate™;
(d) Molecular Probes™ Concanavalin A™ Alexa Fluor® 633 Conjugate™;
(e) Molecular Probes™ Concanavalin A™ Alexa Fluor® 647 Conjugate™;
(f) Molecular Probes™ Concanavalin A™ Fluorescein Conjugate™;
(g) Molecular Probes™ Concanavalin A™ Oregon Green® 488 Conjugate™;
(h) Molecular Probes™ Concanavalin A™ tetramethylrhodamine Conjugate™;
(i) Molecular Probes™ Concanavalin A™ Texas Red® Conjugate™
One or more of these probes may be available from ThermoFisher Scientific Company, Waltham, Mass.

After treatment and immersing, each half-disk specimen is stained with a dye mixture solution of the Fluo-3™, AM™, cell permeant fluorescent probe together with Concanavalin A™, Alexa Fluor® 594 Conjugate probe (containing 5 uM Fluo-3™+5 uM Con-A™ ) for 30 minutes in the dark. After staining, each specimen is immersed into 500-1000 ul PBS solution statically for 2 minutes.

(h) Confocal Laser Scanning Microscopy

The Leica™ TCS SP8 AOBS spectral confocal microscope is used. The confocal system consists of a Leica™ DM6000B upright microscope and a Leica™ DMIRE2 inverted microscope. An upright stand is used for applications involving slide-mounted specimens; whereas the inverted stand, having a 37° C. incubation chamber and $CO_2$ enrichment accessories, provides for live cell applications. The microscopes share an exchangeable laser scan head and, in addition to their own electromotor-driven stages, a galvanometer-driven high precision Z-stage which facilitates rapid imaging in the focal (Z) plane. In addition to epifluorescence, the microscopes support a variety of transmitted light contrast methods including bright field, polarizing light and differential interference contrast, and are equipped with 5×, 20×, 40×, 63× (oil and dry) and 100× (oil) Leica™ objective lenses.

The laser scanning and detection system is described. The TCS SP8 AOBS confocal system is supplied with four lasers (one diode, one argon, and two helium neon lasers) thus allowing excitation of a broad range of fluorochromes within the UV, visible and far red ranges of the electromagnetic spectrum. The design of the laser scan head, which incorporates acousto-optical tunable filters ("AOTF"), an acousto-optical beam splitter ("AOBS") and four prism spectrophotometer detectors, permits simultaneous excitation and detection of three fluorochromes. The upright microscope also has a transmission light detector making it possible to overlay a transmitted light image upon a fluorescence recording.

Leica™ Confocal software LAS AF3.3.0 is used. The confocal is controlled via a standard Pentium PC equipped with dual monitors and running Leica™ Confocal Software. The Leica Confocal Software LAS AF3.3.0 (available from Leica Lasertechnik GmbH, Heidelberg, Germany) provides an interface for multi-dimensional image series acquisition, processing and analysis, that includes 3D reconstruction and measurement, physiological recording and analysis, time-lapse, fluorochrome co-localization, photo-bleaching techniques such as FRAP and FRET, spectral immixing, and multicolour restoration.

(i) Image Analysis

Zn Analysis; The SYTO-9/Zn dye stained samples are chosen to quantify overlap efficiency of red and green pixels. Using the software, the pixel overlap of "green" bacterial probes and that of "red" zinc probes are identified, and then this value is divided by all non-black pixels (that include non-overlapping stannous probes) to provide a co-localization percentage of stannous in bacteria. Generally, the higher this co-localization percentage, the more efficacious the oral care product is in delivering zinc into bacteria.

Ca:EPS; The Fluo-3™/Con-A™ stained specimens, both fluorescence channels are chosen to quantify fluorescence intensity ratio of green pixels (Calcium) to red pixels (EPS) and Con-A™ fluorescence channel is chosen to measure the biofilm thickness. Whereby, six selected fields of Con-A™ fluorescence channel of each specimen are evaluated. These fields are considered as representative of the whole sample after the observer's general examination. The distance is measured from the surface of the biofilm to its base, measuring the thickness of the field, and subsequently the mean thickness of the biofilm of the corresponding specimen is calculated.

Results: Subjects are treated with the Inventive Composition Ex. 3 (i.e., zinc lactate+2% Glycine), Comparative Composition Ex. 2 (i.e., zinc lactate only), an Commercial product Composition Ex. 4 (i.e., Colgate Total™ Whole Mouth Health, Daily Repair toothpaste, containing Zinc Citrate/Zinc Oxide+Arginine), and Control Ex. 1 (PBS) as negative control. The results are provided in Table 2.

TABLE 2

Active Penetration Rate in Biofilm

| Examples | | Biofilm Thickness (um) | Zn Penetration (%) | Total Zinc (ppm) | Soluble Zinc (ppm) | Zn Recovery (%) |
|---|---|---|---|---|---|---|
| Ex. 1 | Phosphate Buffer Solution (artificial saliva) | 35.52 | — | — | — | — |
| Ex. 2 | Zinc Lactate | 13.37 | 62.58 | 2500 | 545 | 83 |
| Ex. 3 | Zinc Lactate + Glycine | 7.14 | 80.01 | 2500 | 510 | 78 |
| Ex. 4 | Zinc Citrate/Oxide + Arginine | 16.755 | 76.50 | 9300 | 1054 | 11 |

*Ex. 4 is a commercial product composition (Colgate Total ™ Whole Mouth Health, Daily Repair toothpaste)

Data is discussed. In reference to Table 2, the fluorescence intensity of Zn within in situ plaque biofilm and average biofilm thickness are measured for various examples and toothpaste formulations are provided. The first column of Table 2 identifies the product with key actives. In turn, each product includes the examples described in Table 1 above (namely examples 2-3) as well as one commercialized products examples 4. Notably example 4 contains zinc citrate and zinc oxide as zinc ion source, and 1.5% of Arginine—a basic amino acid. The second column of Table 2 indicates the dental biofilm thickness. The lower the biofilm thickness, the more effective is the composition. The third column indicates the zinc penetration (%). The higher the percentage, the more effective is the zinc penetration into the biofilm. The fourth and fifth columns indicate the total zinc amount (ppm) and the soluble zinc amount (ppm) present in the examples, respectively. The soluble zinc amount is measured when diluting the example into 3 times of water.

Still referring to Table 2, example 1 ("Ex 1") Phosphate Buffer Solution ("PBS") is used as the negative control. Accordingly, Ex 1 is the least effective (compared to the other compositions) on the impact on dental biofilm thickness. Inventive Ex. 3 shows significantly reduced biofilm thickness and significantly increased zinc penetration compared to the comparative Ex. 2. Notably, Inventive Ex. 3 (containing 2% glycine) even showed significant reduced biofilm thickness, compared with the commercial product Ex. 4 which contains much higher amount of zinc ion, as well as basic amino acid arginine (1.5%).

Example C: Consumer Sensory Test

Consumer Sensory Tests are conducted to measure the preference of consumer towards the Inventive Example 3 vs. the comparative Example 2.

18 trained sensory panelists are instructed for use of a series test product with unawareness of the product identity i.e. brand, ingredients, etc. they are asked to brush teeth using a paired comparison products (2 vs. 3) with randomized brushing order. Each assigned toothpaste is dispensed upon an Oral B Navigator brush and brushed for a controlled 2 minutes, with each panelist recording the sensorial attributes (i.e. regarding astringency) on the standard questionnaire with a 1 to 5 grading score. Table 3 shows the average ranking for Examples 2 and 3. It can clearly showed that addition of the glycine to zinc lactate significantly reduces the noticeable astringency of the dentifrice with 90% confidence level.

TABLE 3

Sensory Results

| | Sensory Panel Grading | |
|---|---|---|
| | Ex. 2 Zinc Lactate | Ex. 3 Zinc Lactate + Glycine |
| Astringency post brushing | 4 | 3 |

*highly astringency 5; mild astringency 3; no astringency 0

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition, comprising:
   a) from 0.2% to 2.0%, by weight of the composition, of a zinc lactate;

b) from about 0.1% to about 6%, by weight of the composition, of a glycine or salt thereof; and c) from 0.05% to 0.5%, by weight of the composition, of a fluoride ion.

2. The dentifrice composition according to claim 1, wherein the dentifrice composition has a pH ranging from 5.0 to 10.5.

3. The dentifrice composition according to claim 1, wherein the dentifrice composition comprises from 500 ppm to 5000 ppm of soluble zinc ion.

4. The dentifrice composition according to claim 1, wherein the dentifrice composition further comprises another zinc ion source selected from the group consisting of zinc citrate, zinc gluconate, and combinations thereof.

5. The dentifrice composition according to claim 1, wherein the dentifrice composition is substantially free of stannous ion source.

6. The dentifrice composition according to claim 1, wherein the fluoride ion is provided by a fluoride ion source selected from the group consisting of sodium fluoride, indium fluoride, amine fluoride, sodium monofluorophosphate, potassium fluoride, zinc fluoride, and combinations thereof.

7. The dentifrice composition according to claim 1, wherein the glycine is present at a level of from about 0.5% to about 5%, by weight of the composition.

8. The dentifrice composition according to claim 1, wherein the dentifrice composition further comprises from 0.01% to 5%, by weight of the composition, of a thickening system, wherein the thickening system is selected from a thickening polymer, a thickening silica, or a combination thereof.

9. The dentifrice composition according to claim 1, wherein zinc penetration within dental biofilm is greater than 50%.

10. The dentifrice composition according to claim 1, wherein the dentifrice composition further comprises from 1% to 35%, by weight of the composition, of an abrasive, wherein the abrasive is selected from a calcium-containing abrasive, a silica abrasive, or a combination thereof.

11. The dentifrice composition according to claim 1, wherein the dentifrice composition further comprises from 1% to 60%, by weight of the composition, of a humectant selected from sorbitol, glycerin, or a combination thereof.

12. A method of treating dental plaque biofilm in a subject, the method comprising the step of brushing the subject's teeth with a dentifrice composition according to claim 1, wherein the brushing occurs at least once a day.

* * * * *